(12) United States Patent
Herrmann

(10) Patent No.: US 7,251,518 B2
(45) Date of Patent: Jul. 31, 2007

(54) BLOOD OPTODE

(75) Inventor: Vera Herrmann, Luebeck (DE)

(73) Assignee: Nirlus Engineering AG, Luebeck (DE)

( * ) Notice: Subject to any disclaimer, the term of this patent is extended or adjusted under 35 U.S.C. 154(b) by 205 days.

(21) Appl. No.: 10/547,024

(22) PCT Filed: Mar. 10, 2004

(86) PCT No.: PCT/DE2004/000470

§ 371 (c)(1),
(2), (4) Date: Aug. 25, 2005

(87) PCT Pub. No.: WO2004/080295

PCT Pub. Date: Sep. 23, 2004

(65) Prior Publication Data

US 2006/0058595 A1    Mar. 16, 2006

(30) Foreign Application Priority Data

Mar. 13, 2003   (DE) ............................... 103 11 408

(51) Int. Cl.
*A61B 5/00*   (2006.01)
(52) U.S. Cl. ...................... 600/322; 600/323; 600/328
(58) Field of Classification Search ................ 600/322, 600/323, 328, 437, 438, 473, 476
See application file for complete search history.

(56) References Cited

U.S. PATENT DOCUMENTS 5,951,481 A    9/1999  Evans
2004/0099815 A1   5/2004  Sfez et al.

FOREIGN PATENT DOCUMENTS

DE         19640807      9/1997
WO        WO 9808076     2/1998

*Primary Examiner*—Eric Winakur
*Assistant Examiner*—Etsub D Berhanu
(74) *Attorney, Agent, or Firm*—Larson & Larson; Herbert W. Larson

(57) ABSTRACT

A method for measuring in non-invasive manner the concentration of blood constituents by which backscattered light is measured under the action of ultrasonic radiation focused towards the inside of a central blood vessel. A light source and detection unit are arranged to detect the backscattered light on the skin surface above the blood vessel. The target tissue is illuminated by two discrete optical wavelengths. An average light intensity distribution is detected over the length of a pulse. The distribution is Fournier transformed, and the largest Fournier components and spectral position are determined in relation to the frequency of the ultrasonic radiation. The component concentration in the blood vessel is calculated taking into account the volume of the ultrasonic focus contributing to the signal and blood flow rate.

6 Claims, 3 Drawing Sheets

BLOOD OPTODE

PRIOR APPLICATIONS

This U.S. §371 National Phase patent application bases priority on International Application No. PCT/DE2004/000470, filed on Mar. 10, 2004, which in turn bases priority on German Application No. DE 103 11 408.4, filed on Mar. 13, 2003.

BACKGROUND OF THE INVENTION

1. Field of the Invention

The invention relates to a medical method and apparatus for measuring in non-invasive manner the concentration of blood constituents, particularly the hemoglobin concentration or oxygenation of the blood in large blood vessels.

2. Description of the Prior Art

Living tissue is largely transparent to electromagnetic radiation in the red and infrared range (wavelength 550 nm<λ<1000 nm). This so called "biological window" is limited towards longer wavelengths by strong absorption bands of water and towards shorter wavelengths by those of hemoglobin. It is in principle possible in this range to "see into" the tissue in depths ranging from a few mm to a few cm.

Over the last decade, so called pulsoximetry has evolved to become one of the most important monitoring methods for observing the patient in the intensive care unit and operating theater. The oxygenation of the blood is measured, i.e. the ratio of the concentration of the oxygen-containing hemoglobin to the total hemoglobin. This involves the measurement of the absorption in transmitted light or remission in backscattered light on tissue with a good blood flow (e.g. fingertip or ear lobe) at two different wavelengths. The wavelengths used are normally around λ=660 nm (where the oxygen-free hemoglobin is much more strongly absorbed than the oxygen-containing hemoglobin) and around λ=940 nm (where the relationships are reversed). During the measurement, use is made of the absorption signal modulation produced by the heart beat. The alternating signal is added to the arterial component of interest, and the absorption by venous blood and tissue to the equisignal present as background. The determination of the oxygenation as a relative quantity is possible with an adequate precision for clinical use, despite certain difficulties in practice.

However, medical literature proves the urgent need for a bedside, i.e. continuous, non-invasive determination of the oxygenation of hemoglobin in large blood vessels. Blood examination in large, so called "central", i.e. heart-near vessels, is impossible with the hereto standard methods for determining oxygenation due to the so called "centralization", (i.e. inadequate blood circulation of the periphery) of emergency patients. There is a need for a method which can be used arterially, e.g. on the internal carotid artery, and if possible, also on large veins, e.g. the internal jugular vein, because the difference in oxygenation provides important information on the oxygen supply of the brain.

The difficulty of a measurement on large blood vessels is that their central position in the body renders a transmission measurement impossible, whereas, remission mainly takes place by diffuse backscattering of photons. A distinction is made between ballistic or quasi-ballistic photons, which are subject to little or no interaction with the tissue, and therefore leave the latter first, and diffuse photons whose path through the tissue is characterized by numerous scattering processes. Ballistic photons are of minor importance for blood analysis. For human tissue, the scattering coefficient $\mu_s$ is much larger than the absorption coefficient $\mu_a$. Thus, $\mu_s$ is typically approximately 10 $cm^{-1}$ so that for layer thicknesses of $\geq 1$-2 mm, no light focus can be produced in the scattering medium. The illumination of lower lying layers consequently takes place quasi-isotropically. The essential problem is the association of backscattered light with a specific location of the scattering.

DE 196 40 807 A1 proposes apparatuses for the detection of diffuse photons which measure in the backscattering direction, i.e. in the vicinity of the light sources, and are used for determining the oxygen concentration in the blood and tissue. Use is made of an empirically known link between the spacing of the exit point of backscattered photons from the entrance point (light source, fiber end) and the average penetration depth of said photons on their path through the tissue for controlling the observation depth through the choice of said spacing.

DE 196 34 152 A1 uses a very similar measuring setup, and the fact that components of the irradiated, coherent light are phase or frequency-shifted by elastic and inelastic scattering processes and are superimposed with the undisturbed components, leads to a speckle pattern. The spatially resolved measurement of the speckle pattern permits an analysis of the exiting stray light with respect to its power spectrum compared with that of the irradiated light. Thus, e.g. through repeated frequency shifts through inelastic scattering on blood, information can be obtained about the average number of scattering processes per photon on the light path through the tissue. The use of a filtering procedure then makes it possible to discriminate photons which have had a predetermined minimum of maximum number of scattering processes, and consequently, have a relatively strong localized penetration depth.

WO 02/08740 A2 describes the advanced prior art for a measuring apparatus with backscattered photons. On the basis of the known interaction of light with the ultrasonic field present in the tissue, conclusions are drawn from the resulting influencing of the phases of the electromagnetic waves with respect to the precise position of the responsible scattering centers in a three-dimensional measuring area. An ultrasonic field suitable for this purpose is produced either by a single movable or a complete array of sound sources in contact with the tissue. What is important for the necessary complex structure of the ultrasonic field is the precise control of the sources with respect to the maintaining of phase delays and repetition times, and/or frequency differences. The extensive data analysis on the detector side is equally complicated. The apparatus is provided for 3D picture-giving tomography in connection with the blood supply of tissue, and is vital for combating tumors.

It is common to all the aforementioned methods that the contribution to the measuring signal of blood from the interior of a large blood vessel cannot be considered in isolation or, in the case of WO 02/08740 A2, can only be established with considerable effort and expenditure. A simple, robust, fast and inexpensive system is necessary for the continuous monitoring of emergency patients. The problem of the invention is to make this available.

SUMMARY OF THE INVENTION

The set problem is solved by the features of claim 1. Advantageous developments of the invention are provided by the subclaims.

The method according to the invention takes up the fundamental idea of WO 02/08740 A2, but does not use any frequency of phase analysis of the light used. Instead, exclusive light intensities are considered, i.e. photons are counted which allows a very simple detector setup and evaluation on the measurement side. It is also unnecessary to use coherent light, although also here standard laser diodes are preferably used.

BRIEF DESCRIPTION OF THE DRAWINGS

Further advantages and features of the present invention can be gathered from the following description of the preferred embodiment relative to the attached drawings, wherein.

DETAILED DESCRIPTION OF THE PREFERRED EMBODIMENT

Figure 1:
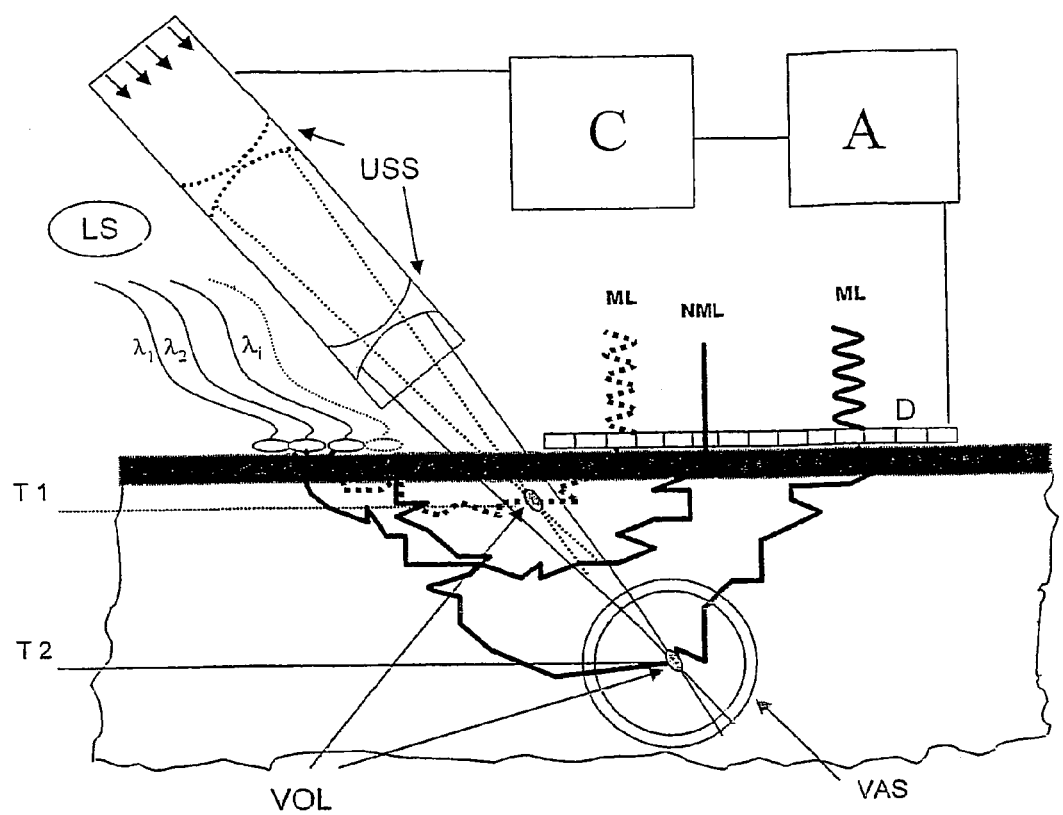
FIG. 1 illustrates a diagrammatic representation of the method and apparatus for performing the method of the present invention.

In FIG. 1, a light source LS emits light, preferably monochromatic light, with one or more discreet wavelengths, e.g. laser light, into the tissue. The light wavelengths $\lambda_1$ to $\lambda_i$ are chosen in such a way that preferably scattering takes place on selected blood constituents, particularly oxygen-rich and oxygen-poor hemoglobin. A significant component of the irradiated light passes out again at a plurality of exit points following numerous scattering processes. A matrix detector D, which comprises flat, juxtaposed, photosensitive pixels which generates an electric signal proportional to the light intensity, is placed on the skin surface in such a way that the detector covers the exit points adjacent to the irradiation point. The detector dimensions must correspond with the sought light penetration depth (see above), i.e. with the depth of the blood vessel examined. An evaluating unit A connected to the detector summates the detector signals and measures the backscattered light intensity leaving the tissue in integrating manner over all the pixels, and over a fixed selected time window. This light intensity is time-constant in the case of constant illumination.

Figure 3:
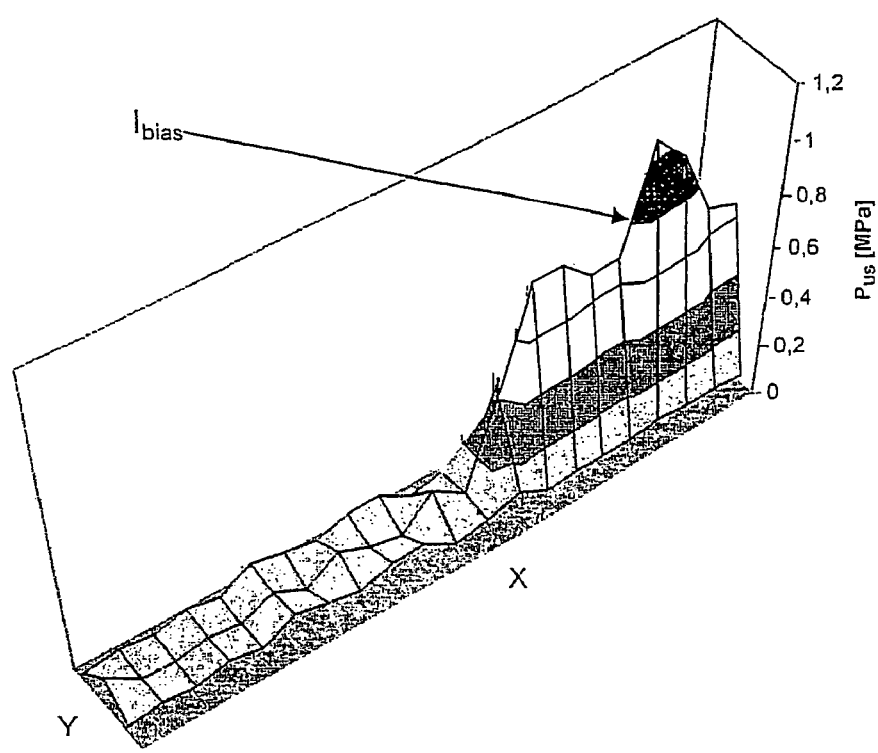
FIG. 3 illustrates the measured pattern of the pressure field of a focused ultrasonic source in a laboratory experiment.

An ultrasonic source USS with adjustable focus now emits additionally pulsed ultrasonic radiation of known frequency $f_{us}$ into the medium. As a result of the focusing, the ultrasonic wave field has a focus spaced from the sound source in which the wave field amplitude is at a maximum. FIG. 3 shows, as an example, the experimentally measured pressure field of a USS in a test tube (diameter 16 mm, Y axis). The X axis covers a spacing range of 44 mm and the pressure $P_{us}$ in the focus assumes a maximum value just above 1 mPa, which corresponds to the medically allowed maximum value.

The ultrasonic irradiation apparatus comprises at least one apparatus for exciting waves USS and an electronic control unit C. The control unit C more particularly controls the ultrasonic frequency, the pulse train and the focus position. The pulse duration and repetition time of the ultrasonic radiation are made much smaller than the time window of the intensity measurement of the backscattered light. The light measurement is triggered with the beginning of each pulse USS and indicates the exiting light intensity over the duration of a pulse. By accumulating the signal over a plurality of pulses, a statistical average is brought about in a few seconds.

By interaction with blood and tissue (local density variations) the ultrasonic wave field gives rise to changes in the optical characteristics, particularly the reflecting/scattering power. As a consequence, the average backscattered light intensity, as a distribution or dispersion over the time interval of a single pulse, contains a component modulated with the frequency $f_{us}$. At the end of the measurement time window, the evaluating unit eliminates the time-constant components of the signal, carries out a Fournier transformation of time to frequency coordinates, and isolates the Fournier component corresponding to $F_{us}$. The Fournier component typically dominates the frequency spectrum and its contribution is the sole remaining measured quantity, referred to as M for short.

Figure 2:
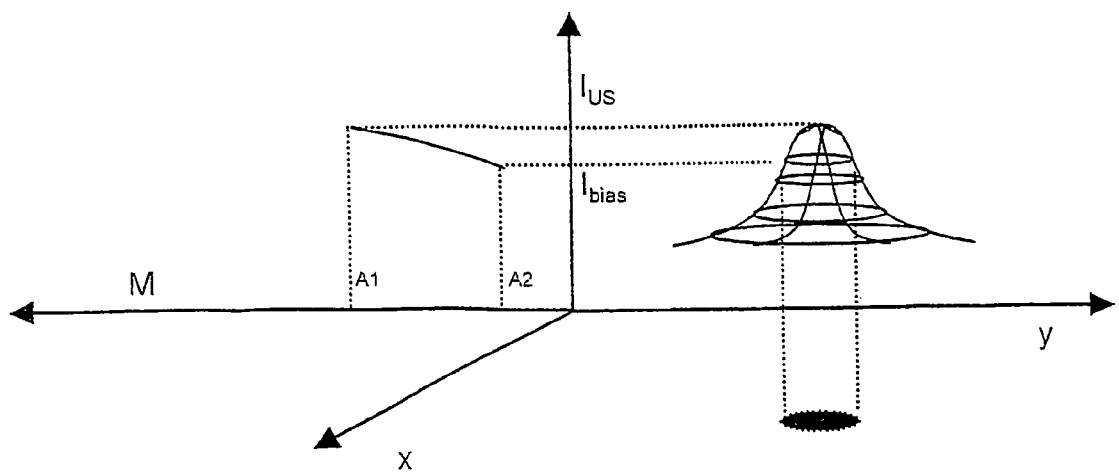
FIG. 2 illustrates the effect permitted by the pinpointing of the scattering centers contributing to the measuring signal of the method and apparatus of the present invention.

M is dependent both on the physical scattering power of the blood for the light wavelengths used and on the amplitude of the ultrasonic wave field $I_{us}$. Experimentally, there is an approximate linear dependence $M(I_{us})$, provided that in the focus $I_{us}$ exceeds a threshold value $I_{bias}$. Otherwise, M is no longer measurable. FIG. 2 diagrammatically illustrates these facts. The spatial configuration of the wave field amplitude is indicated therein by a Gaussian distribution with respect to the coordinates X and Y. M varies between A1 and A2. For a given configuration of the measuring setup (inter-alias sound source, light source, medium, detector resolution, etc.), the value of $I_{bias}$ is fixed and defines the volume of a spatial area in the ultrasonic focus (see also FIG. 3). $I_{us}$ is only above $I_{bias}$ within this area. Signal M results solely from scattering processes from this area.

FIG. 1 shows three exemplified light paths with multiple scattering. Two of the paths pass through the displaceable focus and lead to modulated light intensities ML at the detector D. However, one path does not pass through any focus so that unmodulated light NML enters the detector D and is filtered out by the evaluating unit A.

The ultrasonic focus position is externally preset and is consequently known. The area contributing to the signal measures a few millimeters and can be controlling the sound source in the tissue. The focus can, in particular, be completely located in the interior of a heart-near, large blood vessel. Such a positioning of the focus can be obtained using the Doppler effect. As is known, the interaction of ultrasonics with a medium moving relative to the sound source, and in this case, flowing blood leads to a frequency shift $F_{us} \rightarrow F_{us}^{(D)}$ of the backscattered or reflected wave. This can be recorded by standard ultrasonic sources provided for medical purposes with focus control by skin measurement and used for finding blood vessels VAS (see FIG. 1).

In the case of the above-described Fournier transformation of the time distribution of the light intensity recorded at the detector D, the complete transfer of the focus into a large blood vessel means that the dominant Fournier component occurs at $F_{us}^{(D)}$ instead of $F_{us}$. For a constant scattering capacity of the medium, i.e. when the focus passes from stationary to flowing blood without changing other parameters, the measuring signal M remains unchanged. However, the movement of its spectral position enables conclusions to be drawn concerning the flow rate of the medium (here blood), which for calculating the oxygen concentration, is transferred from the control unit C of the ultrasonic source USS to the evaluating unit A.

Since following the positioning of the focus, the depth of the blood vessel to be observed under the skin surface is known, and the evaluating unit A makes use of this information in order to correct the $F_{us}$-modulated light intensity entering at the detector D in such a way that for the tissue specific absorption and scattering losses per traversed path distance are compensated. Preferably, use is made as the inner reference of the water absorption maximum at ≈975 nm. In particular, preferred manner use is made of the absorption ratio of indocyanine green (ICG) to water, which is dependent of the scattering medium. The thus corrected measuring data makes it possible to decide on absolute values for the optical parameters within the measuring volume defined by the focus. These are separately determined for the different irradiated light wavelengths enabling using known methods to gain conclusions concerning the concentration of the blood constituent to be measured, particularly the ratio of oxygen-rich to oxygen-poor hemoglobin. The procedure described ensures that only blood from the blood vessel of interest is examined.

It is particularly advantageous that the apparatus-preset value for $I_{bias}$ can be mathematically increased on the evaluation side. Thus, the considered volume in the ultrasonic focus can be reduced in planned manner. The precise size of the volume is determinable, and in combination with the also measured blood flow rate, the blood quantity contributing to the measuring unit per unit of time can be calculated in absolute terms.

A preferred development of the method involves examination of vessel wall deposits (plaque). By systematically shifting a sufficiently small focus volume through a large vessel, it is possible to establish whether the focus is wholly or partly in the blood, tissue or another medium. Deposits on vessel walls are prejudicial to the blood circulation and can constitute a life-threatening risk. Different risk potentials are attributed to differently structured deposits. Dangerous heterogeneous deposits must be removed operatively, whereas, homogeneous layers can be tolerated to a certain extent. However, hereto there was no non-invasive differentiating possibility. The presently described method provides information on the structure of the layers, which avoids unnecessary surgery.

Having thus described the invention, what is claimed and desired to be secured by Letters Patent is:

1. A method for the non-invasive measurement of the concentration of blood constituents in central blood vessels, particularly the hemoglobin concentration or oxygenation of the blood, by measuring backscattered light under the action of ultrasonic radiation, the method comprising:
   (a) focusing the ultrasonic radiation on an interior of a central blood vessel;
   (b) presetting a fixed pulse length and repetition time for the ultrasonic radiation;
   (c) arranging a light source and an adjacent detection unit for detecting the backscattered light on a skin surface over the blood vessel in such a way that a spacing between the light source and a plurality of light receptors of the detection unit correspond to a depth of the examined blood vessel;
   (d) illuminating a target tissue with at least two discrete light wavelengths;
   (e) measuring the backscattered light intensity in integrating manner over a surface of the detector and a plurality of ultrasonic pulses;
   (f) determining an average light intensity distribution over a duration of a pulse;
   (g) eliminating time-constant components and carrying out a Fourier transformation of time to frequency coordinates;
   (h) drawing conclusions concerning a blood flow rate and its backscattering power for each of the at least two light wavelengths while determining the blood vessel depth;
   (i) drawing conclusions concerning the quantity of the blood constituents contributing to a signal from the determined backscattering power; and
   (j) calculating concentrations of the blood constituents in the blood vessel while taking account of an ultrasonic focus volume contributing to the signal and the blood flow rate.

2. The method according to claim 1, wherein a volume of a focus contributing to a signal to be measured is reduced on an evaluation side, in that a higher threshold value $I_{bias}$ is required for an ultrasonic wave field amplitude present at least in the target tissue.

3. The method according to claim 2, wherein a focus position is changed in such a way that the focus traverses a central blood vessel continuously or in several steps, the measurement of the backscattered light intensity during the focus movement or at different focus positions being evaluated so as to determine a degree of tissue blood circulation varying with the position.

4. The method according to claim 1, wherein a focus position is changed in such a way that the focus traverses a central blood vessel continuously or in several steps, the measurement of the backscattered light intensity during the focus movement or at different focus positions being evaluated so as to determine a degree of tissue blood circulation varying with the position.

5. The method according to claim 4, wherein Fourier transformation of the average light intensity distribution in a selected spectral range determines the largest contributing Fourier components and their spectral position.

6. The method according to claim 1, wherein Fourier transformation of the average light intensity distribution in a selected spectral range determines the largest contributing Fourier components and their spectral position.

* * * * *